United States Patent [19]
Barnett et al.

[11] Patent Number: 5,769,784
[45] Date of Patent: Jun. 23, 1998

[54] SKIN PERFUSION EVALUATION APPARATUS AND METHOD

[75] Inventors: Richard I. Barnett, Batesville, Ind.; Ryszard S. Ozarowski, Marietta, Ga.; William T. Sutton, Charleston; James M. C. Thomas, Mt. Pleasant, both of S.C.

[73] Assignee: Hill-Rom, Inc., Batesville, Ind.

[21] Appl. No.: 562,781

[22] Filed: Nov. 27, 1995

[51] Int. Cl.$^6$ ............................................. A61B 5/00
[52] U.S. Cl. ........................... 600/300; 600/306; 600/363
[58] Field of Search ..................... 128/630, 632, 128/634–636, 654, 664–666, 691, 736, 742

[56] References Cited

U.S. PATENT DOCUMENTS

| | | |
|---|---|---|
| Re. 30,317 | 7/1980 | Lübbers et al. ........................ 128/635 |
| 2,591,443 | 4/1952 | Larson et al. . |
| 2,855,920 | 10/1958 | Parrot . |
| 3,291,120 | 12/1966 | Karakashian . |
| 3,302,636 | 2/1967 | Clemetson . |
| 3,338,090 | 8/1967 | Coombs, Jr. et al. . |
| 4,267,844 | 5/1981 | Yamanishi . |
| 4,306,569 | 12/1981 | Weil et al. .............................. 128/736 |
| 4,425,921 | 1/1984 | Fujisaki et al. . |
| 4,475,554 | 10/1984 | Hyndman . |
| 4,523,597 | 6/1985 | Sawa et al. . |
| 4,554,930 | 11/1985 | Kress . |
| 4,693,255 | 9/1987 | Beall . |
| 4,699,149 | 10/1987 | Rice . |
| 4,723,554 | 2/1988 | Oman et al. . |
| 4,817,622 | 4/1989 | Pennypacker et al. . |
| 4,859,078 | 8/1989 | Bowman et al. .................... 128/736 X |
| 4,877,034 | 10/1989 | Atkins et al. . |
| 4,894,547 | 1/1990 | Leffell et al. . |
| 5,054,487 | 10/1991 | Clarke . |
| 5,054,502 | 10/1991 | Courage . |
| 5,243,982 | 9/1993 | Mostl et al. . |
| 5,247,940 | 9/1993 | Wilk . |

FOREIGN PATENT DOCUMENTS

0 019 478  11/1980  European Pat. Off. .

OTHER PUBLICATIONS

P. Svedman et al., "A Device for Noninvasive Assessment of Perfusion Pressure in the Skin of Healthy Volunteers", Journal of Investigative Surgery, vol. 2, pp. 479–485, 1989.

H.B. Stoner et al., "Relationships between skin temperature and perfusion in the arm and leg", Clinical Physiology, pp. 27–41, 1991.

Bennett et al., "Vertical Shear Existence in Animal Pressure Threshold Experiments", Decubitus, vol. 1 No. 1, pp. 18–24, Feb. 1988.

Svedman et al., "Epithelialization and Blood Flow in Suction Blister Wounds on Healthy Volunteers", Investigative Surgery, vol. 4, pp. 175–189, 1991.

Julia Anne Ablarde, Queen's University thesis, "Skin Vascular Response to Normal Mechanical Forces", Jul. 1992.

*Primary Examiner*—John P. Lacyk
*Assistant Examiner*—Ryan Carter
*Attorney, Agent, or Firm*—Barnes & Thornburg

[57] ABSTRACT

An apparatus and method for evaluating perfusion adjacent a skin surface includes the steps of measuring a reference rate of perfusion of the skin surface, storing the reference rate of perfusion, and applying a positive force to the skin surface. The apparatus and method also includes the steps of measuring a second rate of perfusion adjacent the skin surface after the positive force is applied, and calculating a differential rate of perfusion between the reference rate of perfusion and the second rate of perfusion after positive force is applied to provide an indication of perfusion adjacent the skin surface. The apparatus and method further includes the step of displaying the indication of perfusion.

11 Claims, 11 Drawing Sheets

SKIN PERFUSION EVALUATION APPARATUS AND METHOD

BACKGROUND AND SUMMARY OF THE INVENTION

The present invention relates to a skin perfusion evaluation apparatus and method. More particularly, the present invention relates to an apparatus and method for rapidly assessing microvascular profusion of the skin which is capable of providing an indication of vascular sufficiency in the tested area.

The apparatus of the present invention is particularly effective in early detection of pressure ulcers to permit treatment before such pressure ulcers (i.e. bed sores) developed. When a patient is bedridden, soft tissue is often compressed for a long period of time between a bone of the patient and a firm surface such as a mattress. This can cause a localized area of tissue necrosis which is a pressure ulcer, decubitus ulcer, or bed sore. The relationship between microvascular blood flow (perfusion) in the skin and an external pressure force applied to the skin is important in the determination of the likelihood of pressure ulcers occurring in the particular tested region.

An object of the present invention is to provide a rapid and non-invasive method for evaluating microvascular perfusion of the skin.

It is known that temperature of the skin resulting from intrinsic or non-environmental factors is primarily produced by blood perfusion. The present invention provides a hand-held mechanism for rapidly assessing perfusion of the skin. The apparatus forces blood from an area of the skin and monitors reperfusion in the area to determine the sufficiency of the perfusion. If blood reperfuses quickly to the area where the pressure has been applied, the patient is less likely to have a pressure ulcer formed in that area. By determining the likelihood for development of pressure ulcers before the pressure ulcers actually occur, it is possible to take preventative steps to prevent pressure ulcers. For instance, the patient could be transferred to a different bed which reduces pressure on the body. The patient can be monitored more closely to make sure that pressure on a particularly vulnerable area is avoided. Therefore, by providing rapid assessment of microvascular perfusion in a particular area, the present invention can reduce the likelihood of development of pressure ulcers, thereby reducing pain and suffering to the patient and reducing costs associated with treating pressure ulcers after they develop.

The apparatus and method of the present invention is also useful for diabetics. The apparatus and method for evaluating skin perfusion can be used to monitor and detect vascular insufficiency in the legs before the insufficiencies lead to leg ulcers and other problems. The apparatus and method of the present invention is useful in any instance where determination of reduced blood flow in an area can result in earlier treatment (i.e. tissue flaps and graphs).

According to one aspect of the present invention, an apparatus is provided for evaluating perfusion adjacent a skin surface. The apparatus includes a housing having first an second interior regions. The housing is configured to engage the skin surface. The apparatus also includes a plunger located in the first region of the housing for applying pressure to a first zone of the skin surface, and a vacuum connection coupled to the second region of the housing to permit suction to be applied to the second region of the housing and to a second zone of the skin surface. The apparatus further includes a first temperature sensor located in the first region for generating an output signal related to the temperature of the first zone of the skin surface, a second temperature sensor located in the second region for generating an output signal related to the temperature of the second zone of the skin surface, and a processor circuit coupled to the first and second temperature sensors for determining a differential temperature between the first and second zones of the skin surface to provide an indication of blood perfusion and vascular sufficiency.

In the illustrated embodiment, the first region of the housing is defined by a central bore for receiving the plunger, and the second interior region of the housing surrounds the first region and the plunger. The apparatus includes a resilient sleeve having a first end coupled to the plunger and a second end coupled to the housing to secure the plunger to the housing for reciprocating movement within the first interior region of the housing. The suction in the second region of the housing automatically forces the plunger downwardly in the first region to engage the first zone of the skin surface located below the first region of the housing.

Also in the illustrated embodiment, the first temperature sensor includes a first plate and a first bank of thermistors located adjacent the first plate for detecting temperature changes in the first plate. The first bank of thermistors is coupled to the processor circuit. The second temperature sensor includes a second plate and a second bank of thermistors located adjacent the second plate for detecting temperature changes in the second plate. The second bank of thermistors is coupled to the processor circuit.

The apparatus includes a display coupled to the processor circuit. Therefore, the processor circuit displays the indication of perfusion on the display. The apparatus may also include a heat source coupled to the processing circuit for heating the skin surface adjacent the housing to a base temperature, or a cooling source coupled to the processing circuit for cooling the skin surface adjacent the housing to a base temperature.

According to another aspect of the present invention, a method is provided for evaluating microvascular perfusion adjacent a skin surface. The method includes the steps of applying a positive force to a first zone of the skin surface, and applying a negative force to a second zone of the skin surface. The method also includes the steps of measuring a microvascular perfusion rate (i.e. rate of perfusion) in the first zone, measuring a rate of perfusion in the second zone, and calculating a differential rate or perfusion between the first and second zones of the skin surface to provide an indication of microvascular perfusion adjacent the skin surface.

Illustratively, the step of measuring the rate of perfusion in the first zone includes the step of measuring a temperature of the skin surface in the first zone, the step of measuring the rate of perfusion in the second zone includes the step of measuring a temperature of the skin surface in the second zone, and the step of calculating a differential rate of perfusion includes the step of calculating a differential temperature between the first and second zones of the skin surface. The method further includes the step of displaying the indication of perfusion.

The second zone of the skin surface may surround the first zone, or the first and second zones of the skin may be spaced apart from each other. The method may also include the step of heating the first and second zones of the skin surface to a base temperature prior to the applying steps, or the step of cooling the first and second zones of the skin to a base temperature before the applying steps.

According to yet another aspect of the present invention, an apparatus is provided for evaluating perfusion adjacent a skin surface. The apparatus includes a housing, and a plunger movably coupled to the housing. The plunger is configured to apply a predetermined pressure to the skin surface. The apparatus also includes a temperature sensor for measuring a temperature of the skin surface below the plunger, and a processor circuit for calculating a differential temperature between a first reference temperature measured by the sensor before pressure is applied to the skin surface by the plunger and a second temperature measured by the sensor after pressure is applied to the skin surface by the plunger. The differential temperature provides an indication of perfusion in the skin surface.

In the illustrated embodiment, the housing has an interior region and a portion of the plunger extends into the interior region of the housing. The apparatus also includes a spring located in the interior region of the housing for applying a biasing force the plunger so that the plunger applies the predetermined pressure to the skin surface.

The temperature sensor may be an infrared transmitter and a thermopile coupled to the processor circuit. In this embodiment, the plunger includes a central passageway defining a wave guide. The infrared temperature sensor is mounted on an end of the plunger in communication with the wave guide. The apparatus further includes a sapphire window coupled to a second end of the plunger spaced apart from the infrared sensor.

The processor circuit provides the indication of perfusion in less than one minute, preferably in less than 30 seconds. The apparatus is a hand held unit and the processor circuit and temperature sensor are operated by a battery. The apparatus includes a display coupled to the processor circuit. The processor circuit provides a visual indication of perfusion on the display. In one embodiment, the processor circuit evaluates a magnitude of the differential temperature to provide the indication of perfusion.

According to still another aspect of the present invention, a method is provided for evaluating perfusion adjacent a skin surface. The method includes the steps of measuring a reference temperature of the skin surface, storing the reference temperature, and applying a positive force to the skin surface. The method also includes the steps of measuring a temperature of the skin surface after the positive force is applied, and calculating a differential temperature between the reference temperature and the temperature after the positive force is applied to provide an indication of perfusion adjacent the skin surface. The method further includes the step of displaying the indication of perfusion.

According to a further aspect of the present invention, a method is provided for evaluating perfusion adjacent a skin surface. The method includes the steps of measuring a reference rate of perfusion of the skin surface, storing the reference rate of perfusion, and applying a positive force to the skin surface. The method also includes the steps of measuring a second rate of perfusion adjacent the skin surface after the positive force is applied, and calculating a differential rate of perfusion between the reference rate of perfusion and the second rate of perfusion after positive force is applied to provide an indication of perfusion adjacent the skin surface. The method further includes the step of displaying the indication of perfusion.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF DRAWINGS

Figure 1:
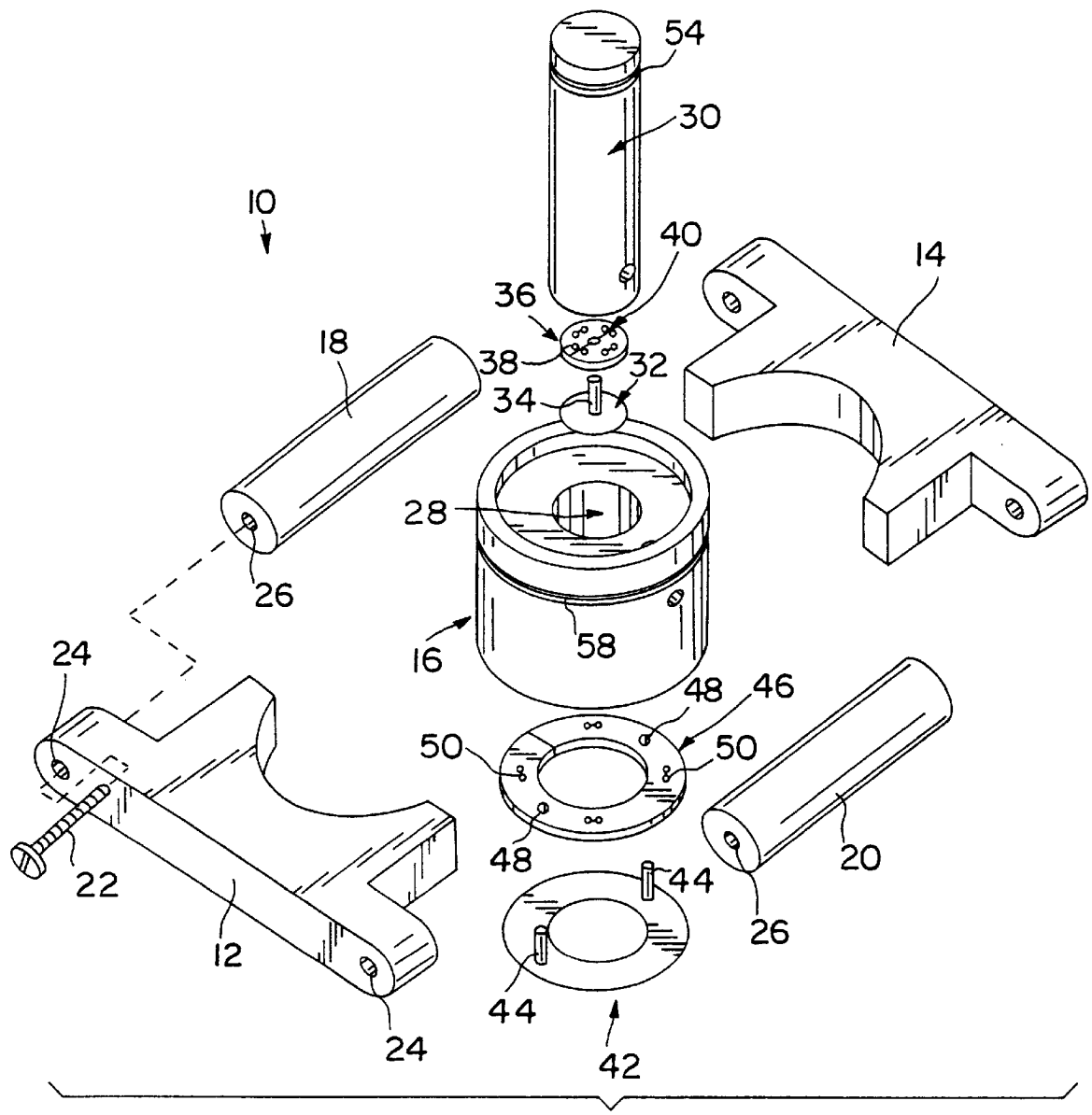
FIG. 1 is an exploded perspective view of a probe assembly of the skin perfusion evaluation apparatus of one embodiment of the present invention.

Referring now to the drawings, FIG. 1 illustrates a probe assembly 10 of one embodiment of the skin perfusion evaluation apparatus of the present invention. Probe assembly 10 includes first and second support members 12 and 14 located on opposite sides of a generally cylindrical body portion or housing 16. Handles 18 and 20 are coupled to support members 12 and 14 by suitable fasteners 22 which extend through apertures 24 formed in support members 12 and 14 and into apertures 26 formed in handles 18 and 20. Housing 16 includes an internal bore 28 for receiving a movable plunger 30 therein. A brass plate 32 is mounted in an end of plunger 30. Brass plate 32 provides an inner temperature sensor plate. A post 34 extends upwardly from plate 32. An internal thermistor holder 36 is formed to include a central aperture 38 which is positioned over post 34. A plurality of thermistors 40 are spaced apart on holder 36. The thermistors 40 are electrically connected to each other to provide an inner temperature sensor. Illustratively, inner thermistor holder 36 is made from Delron.

An outer temperature sensor plate 42 is formed from an annular brass ring. A pair of posts 44 extend upwardly from diametrically opposed portions of sensor plate 42. An outer thermistor holder 46 is also an annular ring. Thermistor holder 46 includes a pair of apertures 48 for receiving posts 44 of sensor plate 42. A plurality of thermistors 50 are positioned in holder 46. Thermistors 50 are electrically coupled together to provide an outer temperature sensor. Outer sensor plate 42 and thermistor holder 46 are coupled to a bottom end of housing 16 surrounding sensor plate 32 and thermistor holder 36 of plunger 30.

Figure 2:
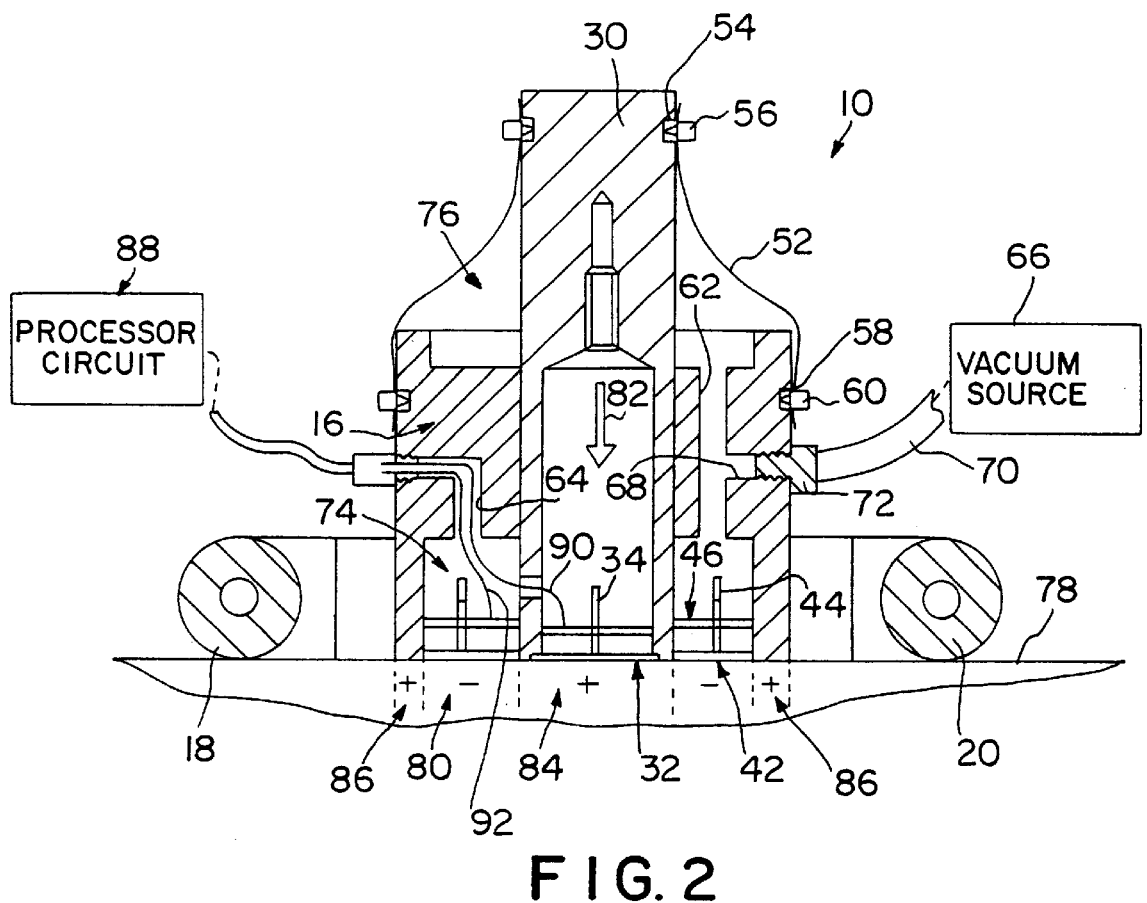
FIG. 2 is a sectional view taken through the probe assembly of FIG. 1.

Further details of the probe assembly 10 are illustrated in FIG. 2. Plunger 30 is coupled to housing 16 by a resilient sleeve 52. A first end of resilient sleeve 52 is coupled to an arcuate groove 54 formed in plunger 30 by a suitable clamp 56. A second end of resilient sleeve 52 is coupled to an arcuate groove 58 formed in housing 16 by a suitable clamp 60.

Figure 3:
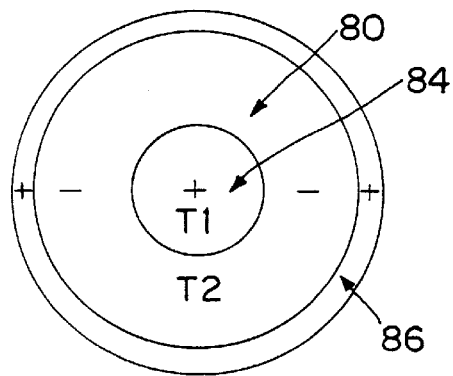
FIG. 3 is a diagrammatical view illustrating the two regions for temperature sensing on a patient's skin using the probe of FIGS. 1 and 2 of the present invention for providing a differential temperature reading for evaluating of skin perfusion.

Housing 16 is formed to include a first passageway 62 and a second passageway 64. A vacuum source 66 is coupled to an inlet 68 of first passageway 62 by a supply line 70 and connector 72, Vacuum source 66 supplies negative pressure or suction to annular lower region 74 above outer temperature sensor plate 42 and outer thermistor holder 46. Vacuum source also supplies negative pressure to the annular region 76 between sleeve 52 and plunger 30. When probe assembly 10 is applied to a skin surface 78 and the vacuum source 66 is turned on, a negative pressure is applied to the skin surface 78 in an outer annular region 80 adjacent outer temperature sensor 42 as illustrated diagrammatically in FIG. 3. The negative pressure in region 76 forces plunger 30 downwardly in the direction of arrow 82. Therefore, plunger 30 applies a positive pressure to skin surface 78 in an inner region 84 also illustrated diagrammatically in FIG. 3. An outer portion of housing 16 applies positive pressure in an annular zone 86 surrounding negative pressure zone 80.

Although zones 80 and 84 are concentric, it is understood that any configuration of the skin zones for pressure and vacuum may be used in accordance with the present invention. The pressure and vacuum zones may be separate areas which are spaced apart on the skin surface 78.

Plunger 30 forces blood away from the skin surface 78 by applying the positive force in the direction of arrow 82. The vacuum source applied to annular zone 80 draws blood toward the skin surface 78 in annular zone 80. The temperature of the skin surface 78 in zone 80 is therefore higher than the temperature of the skin surface 78 in zone 84 since blood is being pulled toward the skin surface 78 in zone 80 and forced away from the skin surface 78 in zone 84.

A processor circuit 88 is configured to measure the differential temperature between zones 80 and 84. The resistance change in inner bank of thermistors 40 which is proportional to the inner temperature is provided by supply line 90. The resistance change of outer bank of thermistors 50 which is proportional to the temperature of outer zone 80 is supplied by line 92.

Figure 4:
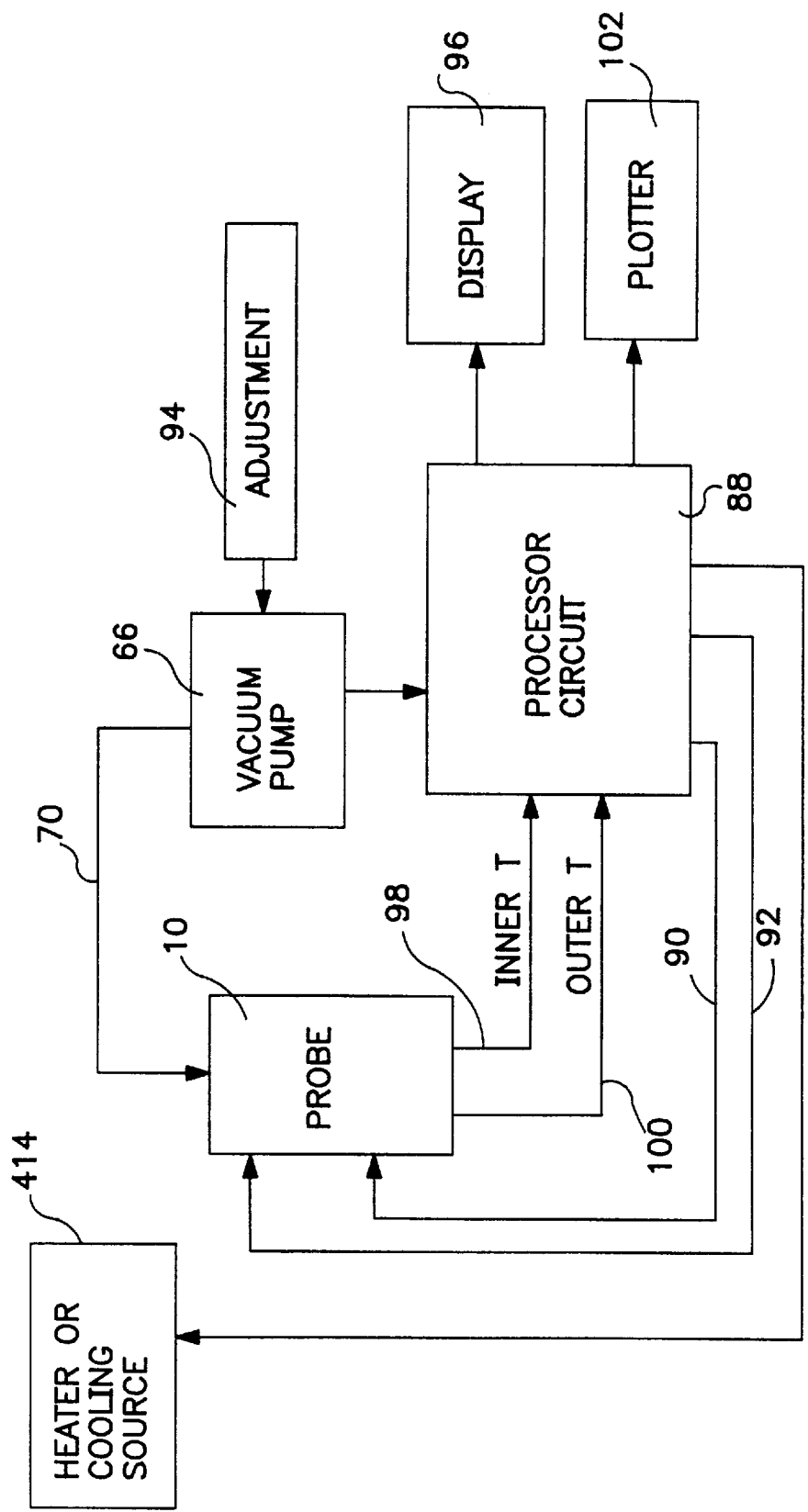
FIG. 4 is a block diagram illustrating further details of the skin perfusion evaluation apparatus.

Further details of the skin perfusion evaluation apparatus are illustrated in FIG. 4. Vacuum pump 66 supplies negative pressure to probe assembly 10 on line 70. The suction applied by vacuum pump 66 is adjustable as illustrated at block 94. Illustratively, vacuum pump 66 is a Model VPO140 vacuum pump available from MEDO U.S.A., Inc. The pressure reading of vacuum pump 66 is output on a display 96. Input signals are provided to the inner bank of thermistors 40 by supply line 90. An electrical signal is supplied to outer bank of thermistors 50 by supply line 92.

Probe assembly 10 transmits a signal proportional to the inner sensor temperature in zone 84 of the skin to processor circuit on line 98. Probe assembly 10 transmits a second signal proportional to the temperature in outer zone 80 from the outer temperature sensor on line 100. Processor circuit 88 measures the differential temperature between the temperature of the outer zone 80 and the temperature of the inner zone 84 over time to calculate the skin perfusion rate as discussed in detail below. Processor circuit 88 provides an output of the differential temperature, the inner absolute temperature, or the outer absolute temperature on display 96. Processor circuit 88 also provides an output of the differential temperature to a plotter or strip chart recorder 102. Illustratively, plotter 102 is a model LM24 plotter available from Linseis, Inc. located in Princeton Junction, N. J.

Figure 5:
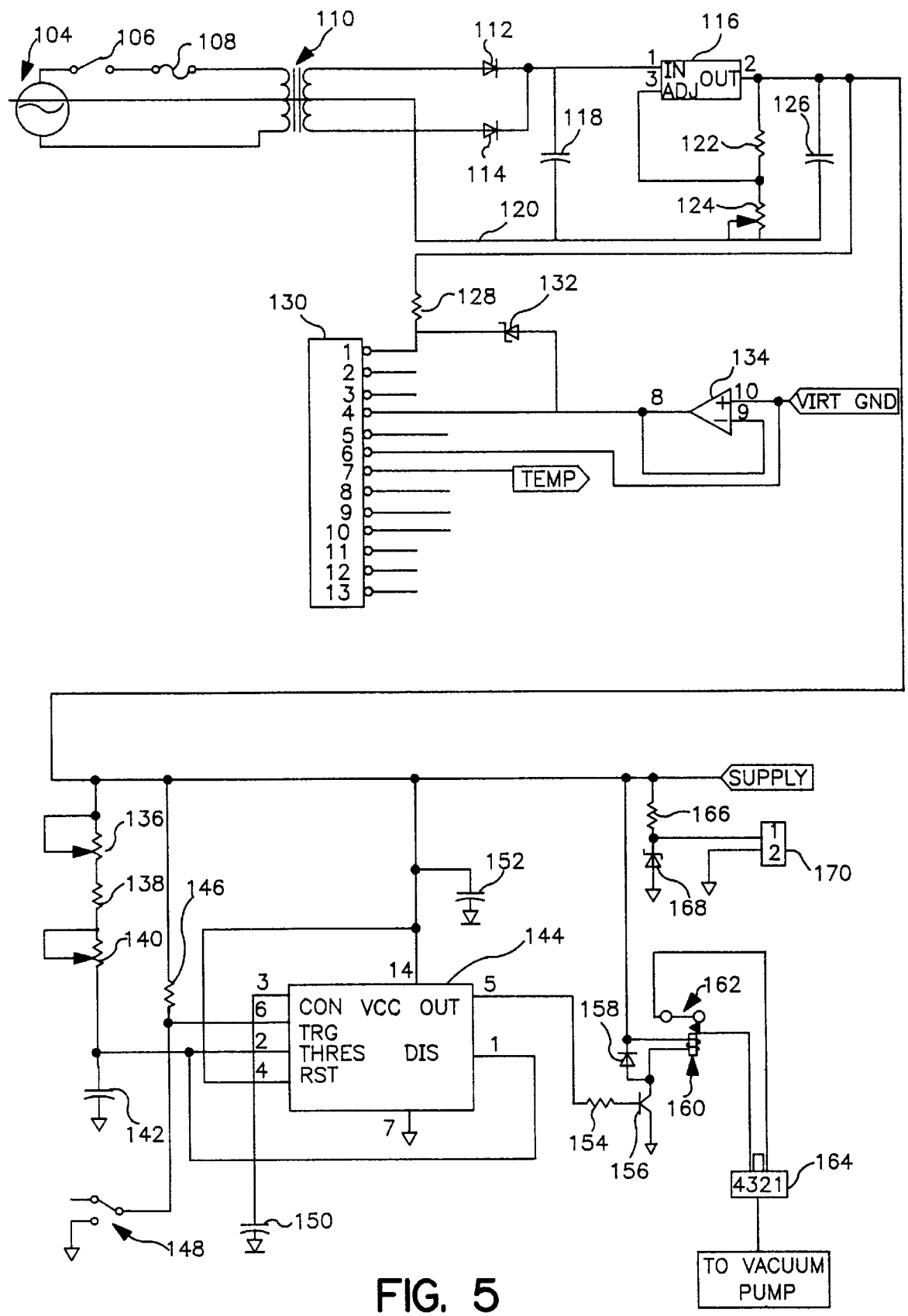
FIG. 5 is a schematic diagram illustrating details of the skin perfusion evaluation apparatus.
Figure 6:
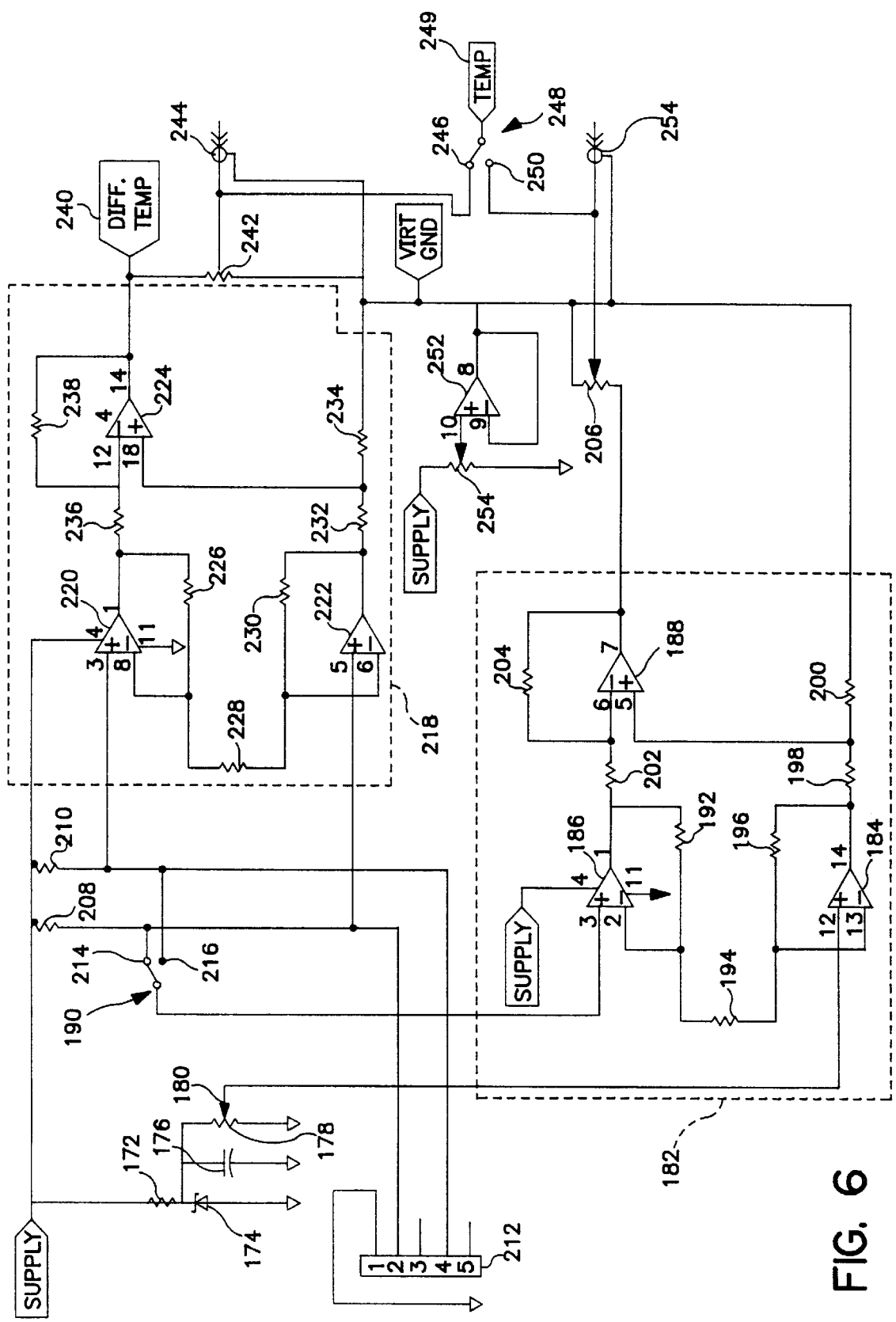
FIG. 6 is a schematic drawing illustrating further details of the skin perfusion evaluation apparatus.

Further details of the processor circuit 88 are illustrated in the schematic diagrams of FIGS. 5 and 6. Referring now to FIG. 5, a standard wall outlet plug 104 for supplying an AC signal to the processor circuit 88 is coupled to an on/off switch 106. Switch 106 is coupled through a fuse 108 to transformer 110. Illustratively, transformer 110 is a 12-volt transformer available from Radio Shack. A first end of a secondary winding of transformer 110 is coupled to an anode of diode 112. A second end of the secondary winding is coupled to an anode of diode 114. The cathodes of diodes 112 and 114 are coupled to an input of a voltage regulator 116. The input of voltage regulator 116 is also coupled through a 10 uF filtering capacitor 118 to a center tap 120 of transformer 110. An output on pin 2 of regulator 116 provides a +9 V supply voltage for the processor circuit. The output of regulator 116 is coupled through a 220-ohm resistor 122 and through a 5k potentiometer 124 to center tap 120. A common terminal of resistor 122 and potentiometer 124 is coupled to the ADJ input at pin 3 of regulator 116. The output of regulator 116 is also coupled through a 0.1 uF capacitor 126 to center tap 120. Illustratively, regulator 116 is a LM317T regulator available from National Semiconductor Corporation.

The output from pin 2 of regulator 116 is also coupled through a 470 ohm resistor 128 to pin 1 of a display connector 130. Illustratively, display connector 130 is a model DPM-102 Big-Little connector available from Modutec. Pin 1 of connector 130 is also coupled to a cathode of a 5.1 V zener diode 132. The anode of diode 132 is coupled to pin 4. Pin 4 of connector 130 is also coupled to an output from pin 8 of an operational amplifier 134. The + input of amplifier 134 is coupled to a virtual ground illustrated in FIG. 6. Virtual ground is also coupled to pin 6 of connector 130. The − input of amplifier 134 is coupled to the output of amplifier 134. A temperature signal input (TEMP) is coupled to pin 7 of display connector 130.

The supply voltage from pin 2 of regulator 116 is also coupled through a potentiometer 136, a 100K resistor 138, a 1M potentiometer 140, and a 220 uF capacitor 142 to ground. The common terminal of potentiometer 140 and capacitor 142 is coupled to a threshold input (THRES) on pin 2 of a timer chip 144. Illustratively, timer 144 is a LM555 timer chip available from National Semiconductor Corporation.

Potentiometer 140 has a control knob on a display panel of the device for adjusting the time interval during which the vacuum pump is actuated. Potentiometer 136 and resistor 138 set the range for the potentiometer to establish minimum and maximum times for the timer.

The supply voltage is also coupled through a 10K resistor 146 to a switch 148. The common terminal of resistor 146 and switch 148 is coupled to a trigger input (TRG) on pin 6 of timer 144. When switch 148 is pressed, the contact moves to ground and draws current through resistor 146 which is supplied to pin 6 of timer 144 to activate the timer and start the vacuum pump 66 and the measurement process.

Pin 1 of timer 144 is coupled to pin 2. Pin 3 of timer 144 is coupled through a 0.1 uF capacitor 150 to ground. Pin 7 of timer 144 is coupled to ground. Pin 14 is coupled to the supply voltage. Pin 14 is also coupled to pin 4. In addition, pin 14 is coupled through a 0.1 uF capacitor 152 to ground. An output of timer 144 on pin 5 is coupled through a 1K resistor 154 to a base of transistor 156. Illustratively, transistor 156 is a 2N2222 transistor available from Motorola. An emitter of transistor 156 is coupled to ground. A collector of transistor 156 is coupled to the supply voltage through the parallel combination of a diode 158 and a relay 160. Illustratively, diode 158 is a 1N914 diode available from Motorola. Relay 160 closes a switch 162 to supply power to a vacuum pump through connector 164 when the transistor 156 is turned on by the timer 144.

The supply voltage is also coupled through a resistor 166 and a 9.1 V zener diode 168 to ground. The common terminal of resistor 166 and diode 168 is coupled to an input of a connector 170. Another input of connector 170 is coupled to ground. Connector 170 provides a supply voltage to a digital manometer display for the vacuum pump 66.

Referring now to FIG. 6, the supply voltage from pin 2 of voltage regulator 116 is coupled through a 1K resistor 172 to the cathode of a 5.1 V zener diode 174. The anode of diode 174 is coupled to ground. The common terminal of resistor 172 and diode 174 is coupled to ground through a capacitor 176. The common terminal of resistor 172 and diode 174 is also coupled to ground through a 5K potentiometer 178. The output of potentiometer 178 on line 180 provides a relatively stable reference voltage supply for an instrumentational differential amplifier 182. Specifically, line 180 is coupled to pin 12 of an operational amplifier 184. Operational amplifiers 184, 186, and 188 are illustratively on a LM324 operational amplifier chip available from National Semiconductor Corporation.

An input to the differential amplifier 182 from switch 190 is coupled to the + input on pin 3 of operational amplifier 186. Pin 4 of operational amplifier 186 is coupled to the supply voltage, and pin 11 is coupled to ground. The output on pin 1 of amplifier 186 is coupled through a 10K resistor 192 to the − input on pin 2 of amplifier 186. The − input of operational amplifier 186 is coupled through a 47K resistor 194 to the − input terminal at pin 13 of amplifier 184. The output on pin 14 of amplifier 184 is coupled through a 10K resistor 196 to the − input of amplifier 184. The output of amplifier 184 is coupled through a 10K resistor 198 and a 10K resistor 200 to virtual ground.

The common terminal of resistor 198 and resistor 200 is coupled to the + input terminal of operational amplifier 188. The − input of operational amplifier 188 on pin 6 is coupled to an output of operational amplifier 186 through a 10K resistor 202. The output on pin 7 of operational amplifier 188 is coupled through a 10K resistor 204 to the − input of operational amplifier 188. The output of operational amplifier 188 is also coupled through a 100K potentiometer 206 to virtual ground.

A bridge circuit includes four resistive legs provided by a 100K resistor 208, a 100K resistor 210, the inner bank of thermistors 38 on plunger 30, and the outer bank of thermistors 50 on outer sensor plate 42. The supply voltage is coupled through resistor 208 to pin 2 of connector 212. The supply voltage is also coupled through resistor 210 to pin 4 of connector 212. Connector 212 is coupled to an electrical hookup of the probe assembly 10 to couple the inner bank of thermistors 38 and the outer bank of thermistors 50 to the bridge circuit. Resistor 208 is coupled to a first terminal 214 of switch 190, and resistor 210 is coupled to a second terminal 216 of switch 190.

The bridge circuit is coupled to another differential amplifier circuit 218. Differential amplifier circuit 218 includes operational amplifiers 220, 222, and 224 which are illustratively on a LM324 operational amplifier chip available from National Semiconductor Corporation. Resistor 210 is coupled to a + input on pin 3 of operational amplifier 220. The supply voltage is coupled to pin 4 of operational amplifier 220, and pin 11 is coupled to ground. An output on pin 1 of operational amplifier 220 is coupled through a 10K resistor 226 to the − input on pin 2 of operational amplifier 220. The − input is also coupled through a 47K resistor 228 to the − input on pin 6 of operational amplifier 222. The + input on pin 5 of operational amplifier 222 is coupled to resistor 208. An output on pin 7 of operational amplifier 222 is coupled through a 10K resistor 230 to the − input terminal of operational amplifier 222. An output of operational amplifier 222 is also coupled through a 10K resistor 232 and a 10K resistor 234 to virtual ground.

The common terminal of resistors 232 and 234 is coupled to the + input on pin 12 of operational amplifier 224. The − input terminal on pin 13 of operational amplifier 224 is coupled through a 10K resistor 236 to the output of operational amplifier 220. The output on pin 14 of operational amplifier 224 is coupled through a 10K resistor 238 to the − input of operational amplifier 224. The output of operational amplifier 224 provides a differential temperature output signal as illustrated at block 240. This signal is proportional to the temperature difference between the inner zone 84 and the outer zone 80 on skin surface 78.

The differential temperature output is coupled through a 100K potentiometer 242 to virtual ground. The differential temperature output is also coupled to a signal line of a coaxial cable connector 244. Connector 244 is coupled via a coax cable to a recorder, an oscilloscope, or another output device. The differential temperature line is also coupled to a first pole 246 of switch 248. The output of switch at block 249 provides a temperature signal (TEMP) and is coupled to pin 7 of the display connector 130 illustrated in FIG. 5. Switch 248 permits either the absolute temperature of inner sensor plate 32 or the temperature of outer temperature sensor plate 42 to be determined based upon the position of switch 190.

Amplifier 252 generates the virtual ground output on pin 8. Amplifier 252 is illustratively a LM324 operation amplifier available from National Semiconductor Corporation. The supply voltage is coupled through a 5K potentiometer 254 to ground. Potentiometer 254 is coupled to a + input on pin 10 of operational amplifier 252. The output of operational amplifier 252 is coupled to the − input terminal on pin 9. The output voltage on pin 8 of operational amplifier 252 is preferably about one-half of the supply voltage. The output voltage from amplifier 252 which provides the virtual ground is about 4 volts. A coaxial cable connector 254 has a signal line coupled to potentiometer 206 and terminal 250 of switch 248. This output provides a voltage proportional to absolute temperature of the selected skin zone.

The output of timer 144, as well as the desired temperature, either differential temperature or absolute temperature, can be supplied to the chart recorder or plotter 102. Therefore, two channels of the chart recorder can be used to compare the temperature during operation of the vacuum pump coupled to timer 144.

Figure 7:
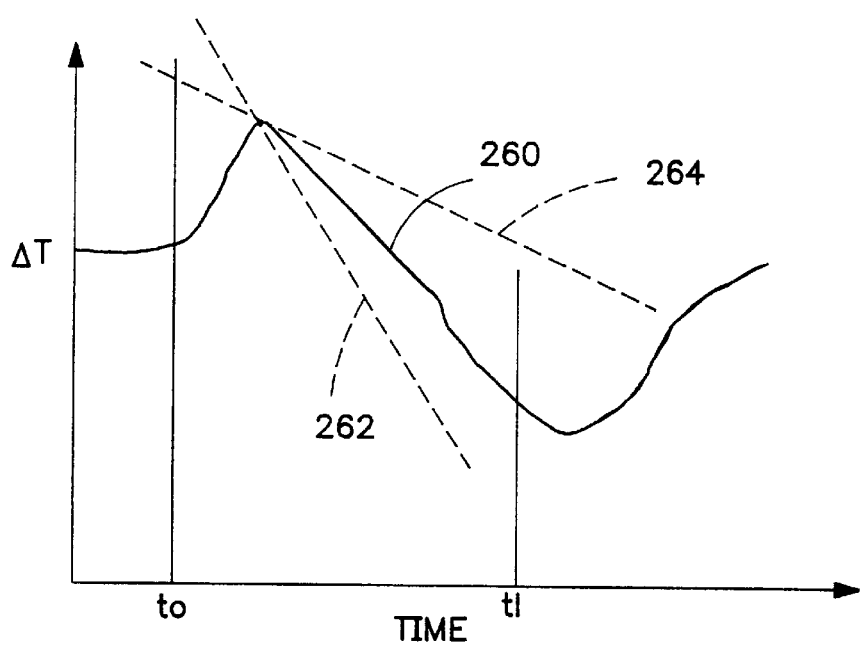
FIG. 7 is a diagrammatical graphic illustration of a differential temperature between the first and second regions of the skin.

FIG. 7 illustrates a plot of the temperature differential between the inner temperature sensor plate 32 and the outer temperature sensor plate 42 over time. The time t0 indicates the time at which the vacuum pump is turned on, and the time t1 indicates the time that the vacuum pump is turned off. Illustratively, the time from t0 to t1 is about 15–30 seconds. The slope of line 260 is proportional to the perfusion rate of the patient. The plunger 30 drives blood out of the region of the skin 84 below plunger 30. The vacuum source draws pressure on region 80 surrounding plunger to draw blood toward the skin surface 78. Patients with better circulation will have a rapidly changing differential temperature when suction is applied. Therefore, for patients with better circulation such as very young children, the slope of line 260 will be greater, indicating better skin perfusion as illustrated by dotted line 262. For patients with poor circulation, the slope of line 260 will be less as illustrated by dotted line 264.

Figure 8:
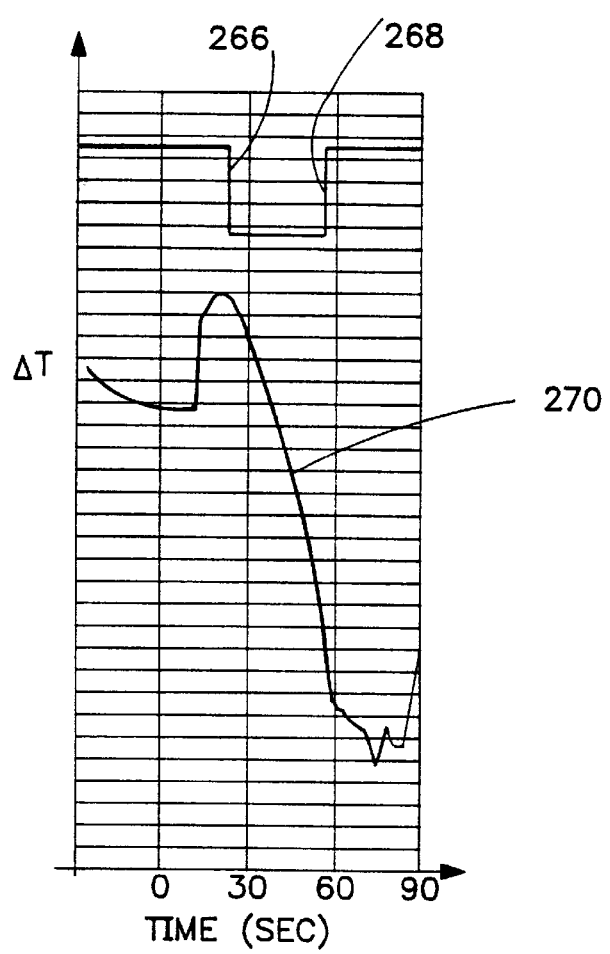
FIG. 8 is a sample strip chart recording for the differential temperature measured by the apparatus of the present invention for a three month old girl.

FIG. 8 illustrates a plot for a three month old girl with the probe assembly 10 located on an anterior abdomen. Line 266 indicates the vacuum pump on and line 268 indicates the vacuum pump off. The plot of differential temperature has a large slope and a large amplitude change during the time the vacuum pump is on. This indicates excellent skin perfusion.

Figure 9C:
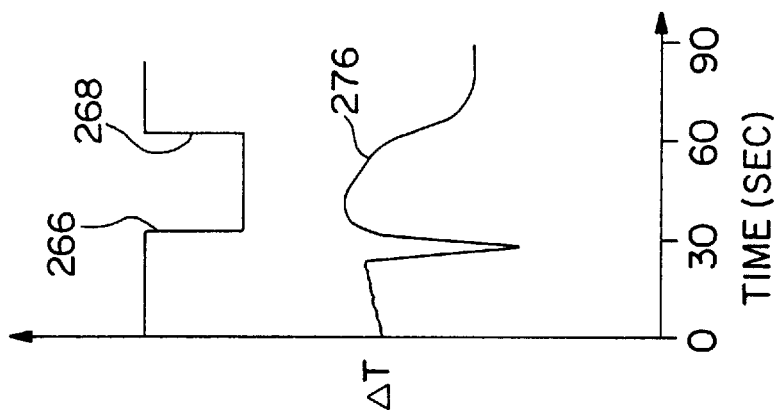
FIGS. 9a–c are sample strip chart recordings under various conditions of the differential temperature measured on a healthy 25-year-old male.
Figure 9B:
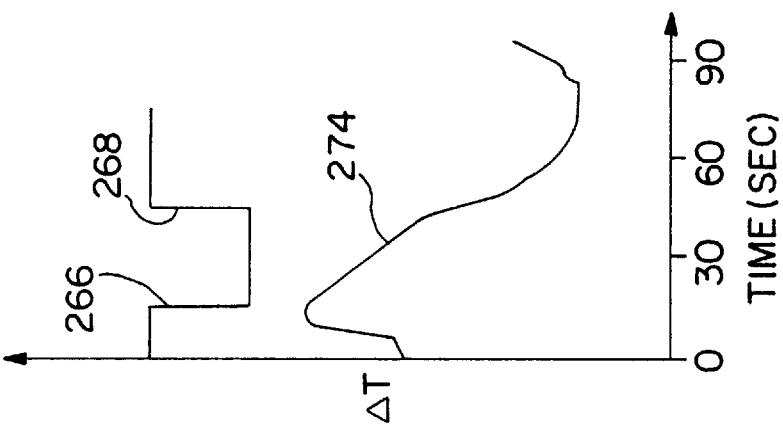
Figure 9A:
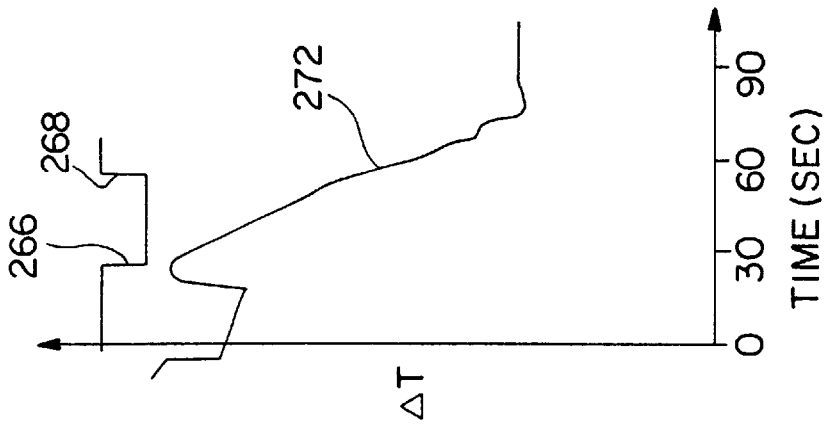

FIGS. 9a, 9b, and 9c indicate three tests done on a healthy 25-year-old male. The probe assembly 10 was located on a left forearm of the subject. FIG. 9a illustrates a plot of the temperature differential 272 during an initial test with no restriction of blood flow to the subject's arm. The test illustrated in FIG. 9b was taken after a blood pressure cuff was attached to an upper left arm of the subject for 1 minute. The blood pressure cuff had 140–160 mmHg pressure. The plot of differential temperature over time is illustrated by line 274. There is a substantial decrease in slope and a substantial decrease in the total amplitude change of the differential temperature for plot 274 compared to the initial plot 272 in which blood flow was not restricted.

FIG. 9c is a plot for the same subject after the blood pressure cuff at 140–160 mmHg pressure was applied for 4 minutes. Blood flow has therefore been substantially reduced to the left forearm. Again, plot 276 has a substantially reduced slope and a substantially reduced total amplitude change over the time period during which the vacuum pump 66 was actuated as compared to both previous plots 274 and 272.

Both the slope and amplitude change of the differential temperature plots during application of the vacuum source are related to microvascular perfusion of the skin. Such microvascular perfusion provides an indication for early diagnosis of skin diseases which can be treated by known support equipment and beds. There is a correlation between microvascular perfusion and the etiology of pressure ulcers. The present invention provides an apparatus for rapidly evaluating a patient's microvascular perfusion. If reduced skin perfusion is detected, treatment can be initiated earlier to reduce the likelihood of further skin degradation and pressure ulcers.

In operation, power switch 106 is turned on and probe assembly 10 is positioned on the skin. Preferably, temperature readout on display 96 is monitored until the temperature stabilizes. Switch 148 is then pressed to initiate the vacuum pump 66. The differential temperature rises and then stabilizes after time. This temperature differential between the inner skin zone 84 and the outer skin zone 80 is either plotted on plotter 102 or processed using another processor circuit 88 which includes a microprocessor to analyze the slope and amplitude change of the temperature differential during application of the vacuum 66. After a predetermined time, the vacuum pump 66 shuts off. The probe may be maintained in contact with the skin to observe temperature stabilization.

Figure 10:
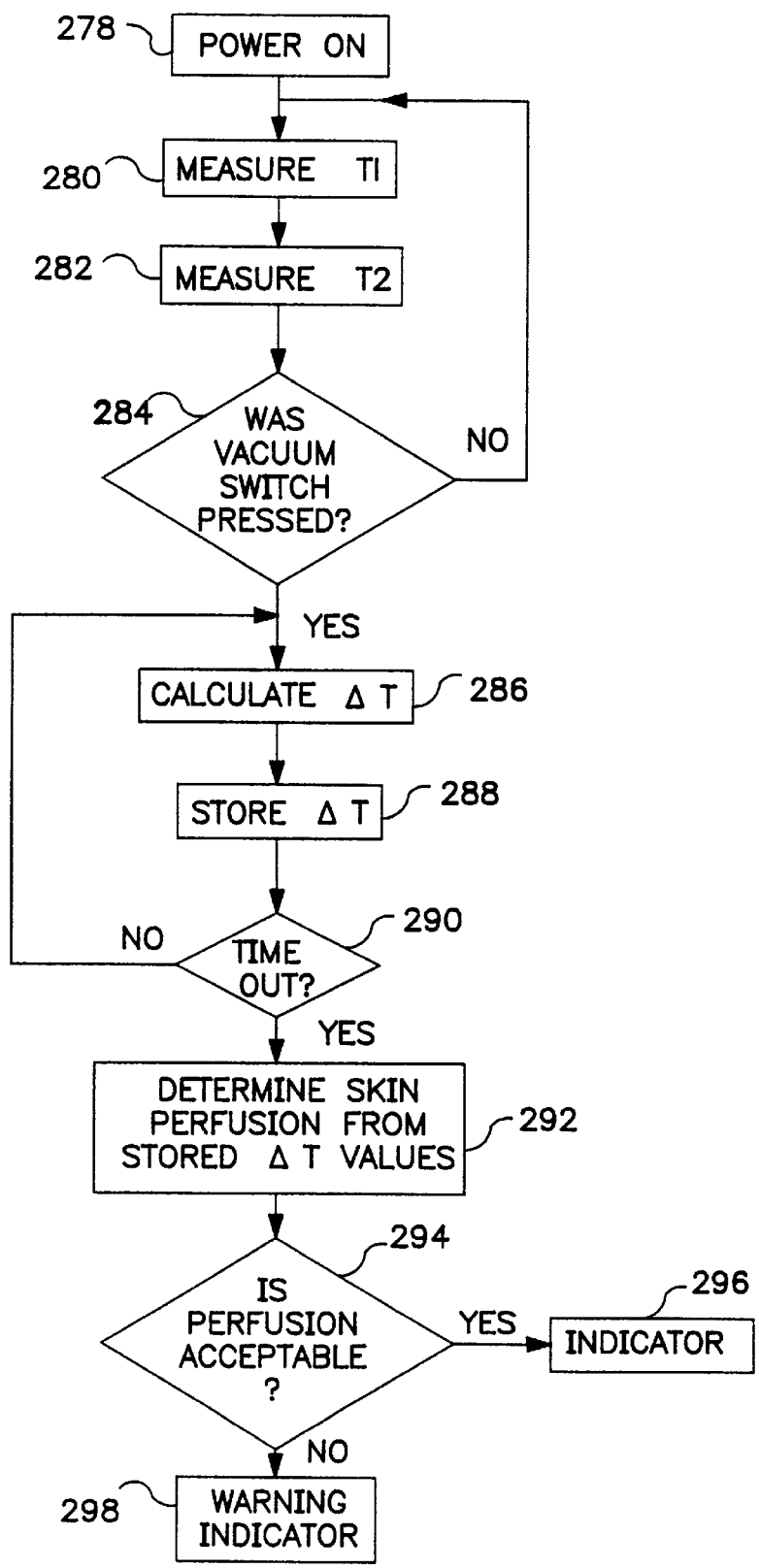
FIG. 10 is a flow chart illustrating the steps performed by the apparatus of FIGS. 1–6 to evaluate skin perfusion.

Details of the operation of processor circuit 88 which includes a microprocessor to measure skin perfusion are illustrated in FIG. 10. Power switch 106 is turned on as illustrated at block 278. A first temperature measurement from the vacuum skin zone 80 is taken at block 280. A second temperature measurement from the pressure skin zone 84 is taken at block 282. The processor circuit determines whether the switch 148 was pressed at block 284. If not, the processor circuit continues to measure the temperatures in both the adjacent pressure and vacuum skin zones at blocks 280 and 282.

If the switch was pressed at block 284, the processor circuit calculates a differential temperature between the pressure and vacuum skin zones 84 and 80 on the skin surface 78 as illustrated at block 286. The differential temperature is stored as illustrated at block 288. The processor circuit then determines whether the evaluation time has expired at block 290. If not, the processor circuit returns to block 286.

Once the time has expired at block 290, the processor circuit evaluates the skin perfusion rate from the stored differential temperature values as illustrated at block 292. This determination can be made from the amplitude change in the differential temperature or from measurements of the slope of the change during the time period of application of the vacuum.

The processor circuit determines whether the skin perfusion rate is acceptable at block 294. Comparison can be made to a table of stored values or to a preset minimum for the amplitude change or slope of the differential temperature values. If the processor circuit determines that the skin perfusion rate is acceptable, an indicator is provided at block 296 on display 96. This indicator advises the caregiver that the tested skin region has an acceptable perfusion rate. If the skin perfusion rate in the tested area is not acceptable at block 294, a warning indicator is provided on display 96 as illustrated at block 298. If desired, a quantitative rating of skin perfusion may be provided based upon the calculation of the differential temperature and the comparison to the table. For instance, a normal rating, a marginal rating, and a poor rating may be selectively provided on the display to indicate the relative level of skin perfusion in the tested area. Any type of quantitative value may be used.

Figure 11:
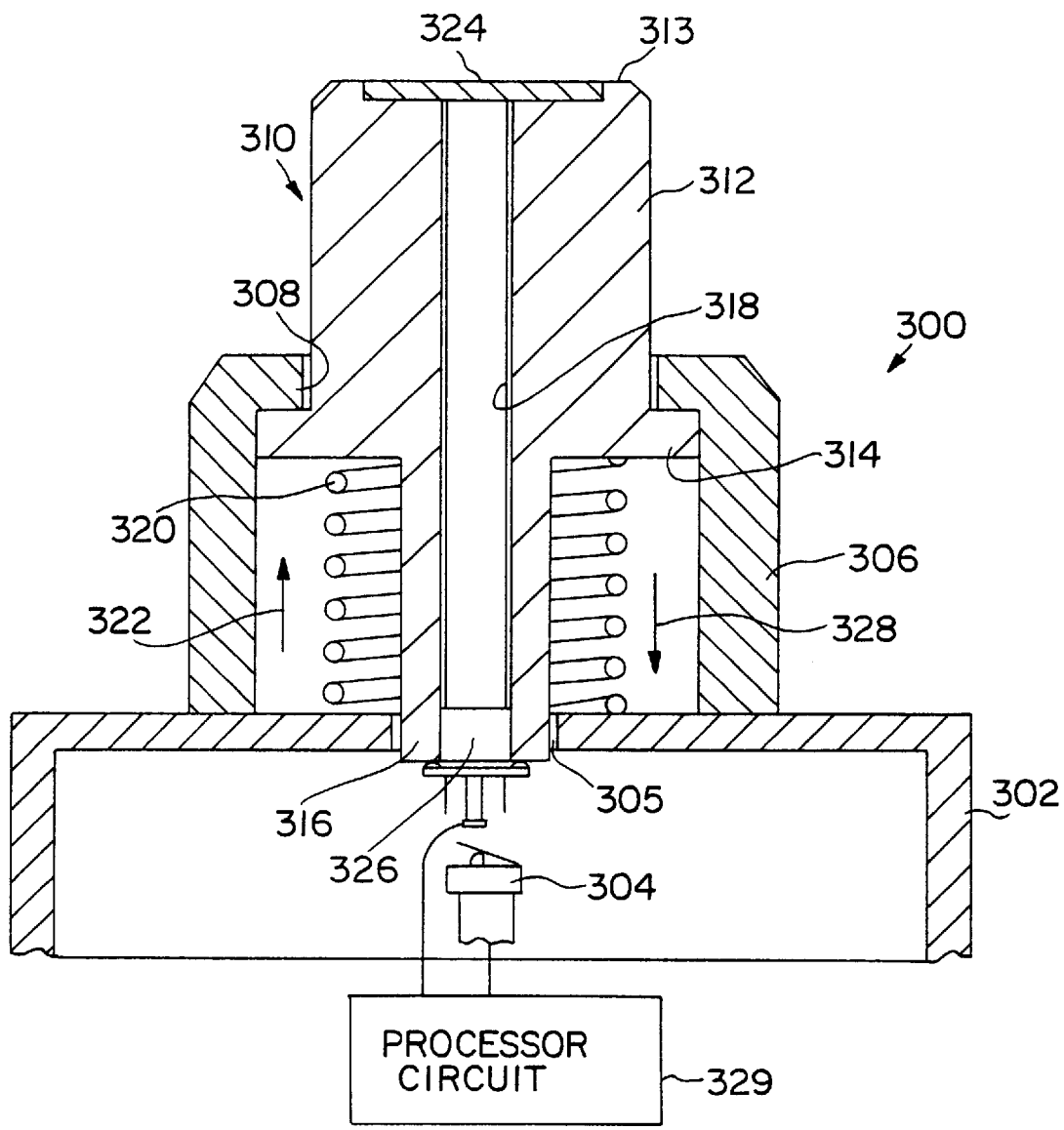
FIG. 11 is a sectional view of another embodiment of the present invention which includes an infrared temperature sensor to evaluate skin perfusion.

Another embodiment of the present invention uses an infrared (IR) sensor for detecting temperature changes of the skin. The probe assembly for the IR sensor embodiment is illustrated in FIG. 11. Probe assembly 300 includes an enclosure 302 having an activation switch 304 located therein. Enclosure 302 includes a top aperture 305. A housing 306 is coupled to enclosure 302 over aperture 305. Housing 306 includes a central aperture 308. A plunger 310 having a head portion 312 with a top face 313, a flange 314, and an extended portion 316 is located partially within housing 306. Plunger 310 is formed to include a central passageway 318 which is lined with a reflective material to form an infrared wave guide. A calibrated spring 320 is located within housing 306 to bias plunger 310 in the direction of arrow 322. A sapphire window 324 is located in a recessed portion of front face 313 of head 312 over a first end of infrared wave guide 318. An infrared sensor 326 is coupled to a second end of the infrared wave guide 318. The infrared sensor 326 faces the sapphire window 324 mounted at an opposite end of plunger 310. The infrared sensor 326 includes an infrared transmitter and a thermopile which converts temperature or radiant energy reflected back from the skin surface to electrical power proportional to the skin surface 78 temperature.

In operation, sapphire window 324 engages a skin surface 78. The entire probe assembly 300 is then moved in the direction of arrow 322 toward the skin surface 78. This causes movement of plunger 310 in the direction of arrow 328 against the spring force of the calibrated spring 320. Movement of plunger 310 in the direction of arrow 328 causes switch 304 to be activated. The switch 304 sends a signal to a microprocessor 330 as discussed below with reference to FIG. 12. Plunger 310 applies a predetermined pressure to the skin surface 78 as established by the spring constant force of the calibrated spring 320, the surface area of front face 313, and the travel distance of the plunger needed to activate the switch 304.

Figure 12:
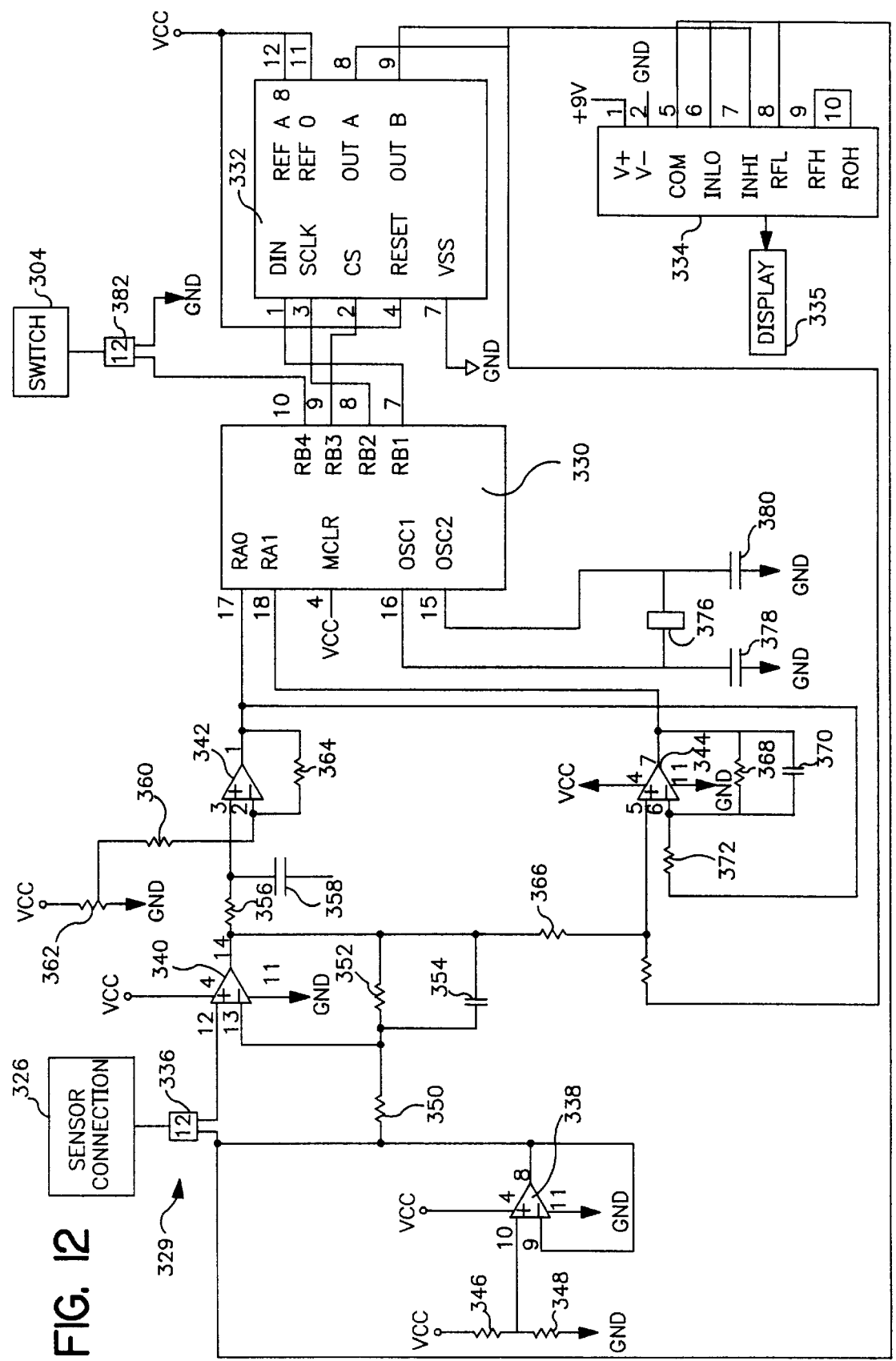
FIG. 12 is a schematic diagram of the control circuitry of the embodiment of the invention illustrated in FIG. 11.

A processor circuit 329 is coupled to switch 304 and to IR sensor 326. Processor circuit 329 is located within enclosure 302. Details of processor circuit 329 are illustrated in FIG. 12. Processor circuit includes a microprocessor 330, a digital-to-analog converter 332, and a display connector 334. Illustratively, microprocessor 330 is a PIC16C71 microprocessor available from Microchip Technology, Inc. Digital-to-analog converter 332 is illustratively a MAX512 converter available from Maxim Integrated Products, Inc. Display connector 334 is illustratively a model DPM-102 Big-Little connector available from Modutec.

The output from the thermopile of IR temperature sensor 326 is coupled to a connector 336. A first pin of connector 336 is coupled to pins 5, 6, and 8 of display connector 334. The first pin of connector 336 is also coupled to an output on pin 8 of operational amplifier 338. Illustratively, operational amplifiers 338, 340, 342, and 344 in FIG. 12 are on a LM324 quad operational amplifier chip available from National Semiconductor Corporation.

A VCC supply voltage for FIG. 12 is illustratively +5 V. A voltage regulator reduces a +9V battery output to the required +5V supply. Therefore, an AC power outlet is not required to operate probe assembly 300. Supply voltage VCC is coupled through a resistor 346 and a capacitor 348 to ground. A common terminal of resistor 346 and capacitor 348 is coupled to the + input on pin 10 of operational amplifier 338. Pin 4 of operational amplifier 338 is coupled to VCC, and pin 11 is coupled to ground. The output of operational amplifier on pin 8 is coupled to the − input on pin 9.

Pin 1 of connector 336 is also coupled through a 150 ohm resistor 350 to the − input on pin 13 of operational amplifier 340. The + input on pin 12 of operational amplifier 340 is coupled to pin 2 of connector 336. Pin 4 of operational amplifier 340 is coupled to VCC, and pin 11 is coupled to ground. An output on pin 14 of operational amplifier 340 is coupled through the parallel combination of a 100 k resistor 352 and a 0.1 uF capacitor 354 to the − input of operational amplifier 340.

The output on pin 14 of operational amplifier 340 is coupled through a resistor 356 to the + input on pin 3 of operational amplifier 342. The + input of operational amplifier 342 is also coupled through a capacitor 358 to ground. The − input on pin 2 of operational amplifier 342 is coupled through a resistor 360 to potentiometer 362. An output on pin 1 of operational amplifier 342 is coupled through a resistor 364 to the − of operational amplifier 342. The output of operational amplifier 342 is also coupled to an analog-to-digital input on pin 17 of microprocessor 330.

The output of operational amplifier 340 is also coupled through a 15 k resistor 366 to the + input on pin 5 of operational amplifier 344. Pin 4 of operational amplifier 344 is coupled to VCC, and pin 11 is coupled to ground. An output on pin 7 of operational amplifier 344 is coupled through the parallel combination of a 15K resistor 368 and a 0.1 uF capacitor 370 to the − at pin 6 of operational amplifier 344. The output on pin 1 of operational amplifier 342 is also coupled through a 4.7K resistor 372 to the − of operational amplifier 344. The + input of operational amplifier 344 is coupled through a 4.7K resistor 374 to a first output on pin 8 of digital-to-analog converter 332. An output on pin 7 of operational amplifier 344 is coupled to a second analog-to-digital input on pin 18 of microprocessor 330.

Pin 4 of microprocessor 330 is coupled to VCC. Pins 15 and 16 of microprocessor 330 are coupled to an oscillator 376 and capacitors 378 and 380. Pin 7 of microprocessor 330 is coupled to pin 1 of converter 332. Pin 8 of microprocessor 330 is coupled to pin 3 of converter 332. Pin 9 of microprocessor 330 is coupled to pin 2 of converter 332. Pin 10 of microprocessor 330 is coupled to a first pin of connector 382. A second pin of connector 382 is coupled to ground. Connector 382 is coupled to switch 304.

Pins 4, 11, and 12 of converter 332 are coupled to VCC. Pin 7 of converter 332 is coupled to ground. A second output from pin 9 of converter 332 is coupled to an input on pin 7 of display 334. Pin 1 of display 334 is coupled to a +9V supply voltage. Pin 2 of display 334 is coupled to ground. Pins 9 and 10 of display 334 are coupled together.

In operation, operational amplifier 338 provides a virtual ground voltage level needed for the operational amplifier section. Operational amplifier 340 is connected to the output of the thermopile of IR temperature sensor 326. The output from sensor 326 is amplified and filtered by operational amplifier 340 to a usable level. The output from operational amplifier 340 is passed through a low pass filter provided by resistor 356 and capacitor 358 to operational amplifier 342. Operational amplifier 342 provides offset adjustment control through potentiometer 362. The output of operational amplifier 342 is applied to the analog-to-digital converter input on pin 17 of microprocessor 330.

Microprocessor 330 constantly reads the value of the voltage on pin 17 and sends this signal to the digital-to-analog converter 332. An output of converter 332 on pin 8 is coupled to the − input of operational amplifier 344. The output of operational amplifier 342 is coupled to the − of operational amplifier 344 as discussed above. Therefore, the microprocessor 344 maintains the difference between the positive and negative inputs to operational amplifier 344 close to zero.

The microprocessor 330 stops updating the value of the digital-to-analog converter input on pin 17 as soon as switch 304 changes state. The output voltage of amplifier 344 then reflects temperature changes referenced to a previous reference value held constant by the microprocessor 330. This output voltage from operational amplifier 344 is supplied to the second analog-to-digital input at pin 18 of microprocessor 330. Microprocessor 330 subtracts the two values from pins 18 and 17 to determine a differential temperature between the detected temperature after activation of switch 304 when pressure is applied by plunger 310 and the initial temperature reading. This differential temperature is supplied to an input of digital-to-analog converter 332. The output voltage on pin 9 is used to drive a display through connector 334. By detecting a slope and/or an amplitude change in the differential temperature, the microprocessor 330 can calculate skin perfusion on the patient. The magnitude of the temperature difference is a measure of the vitality of tissues and skin perfusion in the test subject.

Figure 13:
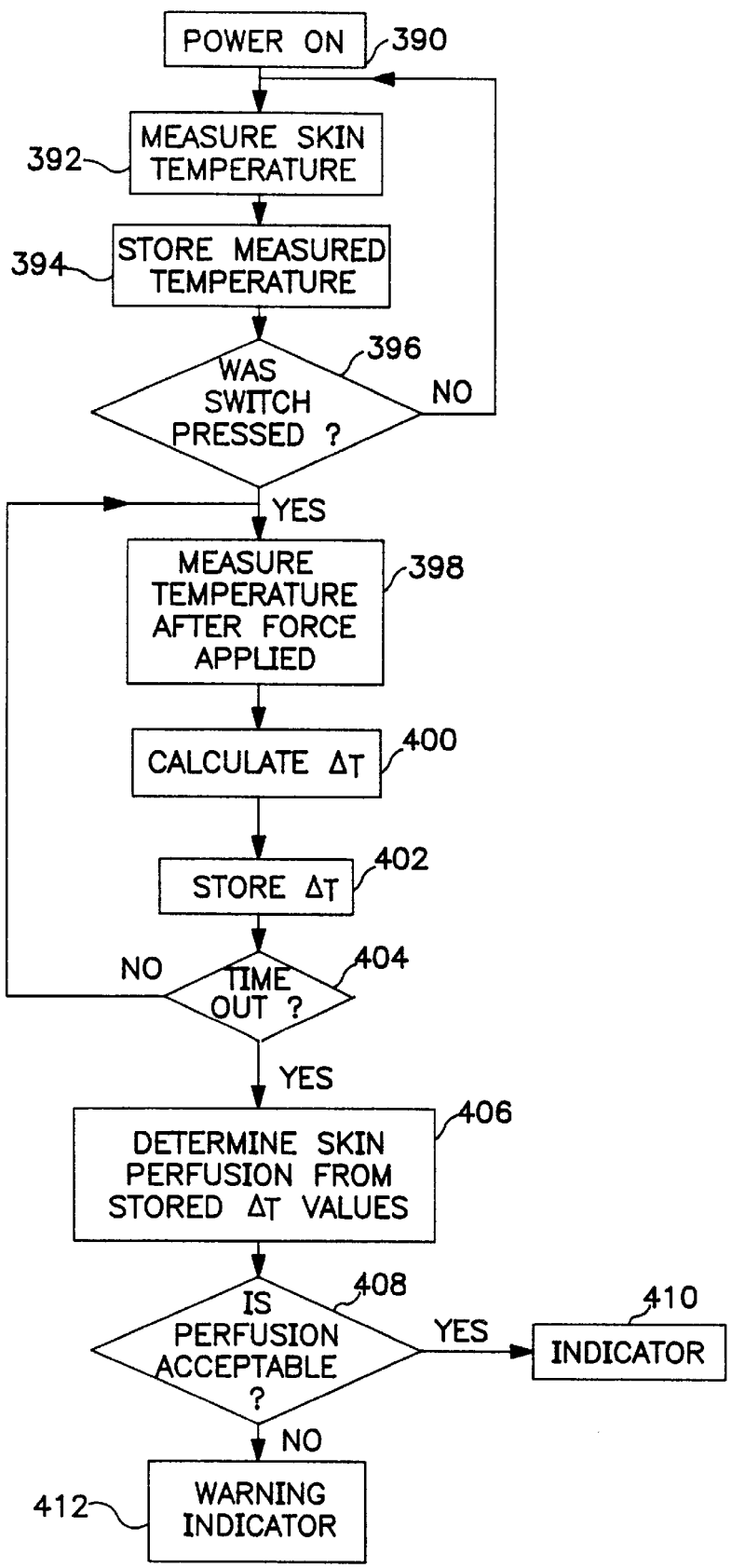
FIG. 13 is a flow chart illustrating the steps performed by the second embodiment of FIGS. 11 and 12 to evaluate skin perfusion.

Operation of the second embodiment of the present invention is illustrated in FIG. 13. Power to the device is turned on as illustrated as block 390. The IR sensor 326 provides a signal indicative of the skin temperature to the microprocessor 330 as indicated as block 392. The initial skin temperature measured at block 392 before pressure is applied is stored at block 394 for use as a reference temperature. Microprocessor 330 determines whether switch 304 was pressed at block 396. If not, microprocessor 330 returns to block 392.

If switch 304 was pressed, a new temperature measurement is taken after plunger 310 engages the skin surface 78 and forces blood away from the skin surface to reduce the temperature. This measurement step is illustrated at block 398. Microprocessor 330 then calculates the differential temperature between the temperature measured at block 398 and the stored reference temperature from block 394. This step is illustrated at block 400. Microprocessor 330 stores the differential temperature as illustrated at block 402. Microprocessor 330 determines whether a time out has occurred at block 404. If not, microprocessor 330 returns to block 308 to continue measuring the temperature of the skin surface.

After the time out occurs, the microprocessor 330 determines or evaluates skin perfusion from the stored differential temperature values as illustrated at block 406. The magnitude of the differential temperature calculated at block 400 is a measure of the vitality of tissues in the skin or skin perfusion. Microprocessor 330 determines whether skin perfusion is acceptable at block 408. For instance, the microprocessor can compare the maximum differential temperature value to a stored reference table to determine whether the skin perfusion rate is acceptable. If the rate is acceptable, microprocessor provides an indicator signal at block 410. If the skin perfusion rate is not acceptable, the microprocessor generates a warning signal on display 335 as illustrated at block 412. The output can be a simple "yes/no" indication as to whether skin in the tested area has an acceptable perfusion rate. A quantitative output can also be generated based on the table. For instance, a normal, marginal, or poor perfusion rating may be displayed based on the table comparison. A numerical representation of the skin perfusion rate may also be displayed.

The temperature sensors provide a method of detecting volume of blood flow per volume of tissue per time. If is understood that other techniques such as Laser Doppler sensing, or any other technique for measuring rate of perfusions may be used in accordance with the present invention.

If desired, a separate heater or cooling source may be provided on probes 10 and 300 to heat or cool the skin surface in the test area. The heating and cooling unit provides a base temperature for the skin surface to enhance observations of the skin surface for evaluation perfusion. The heater or cooling source 414 is diagrammatically illustrated in FIG. 4.

A caregiver can use the results of the skin perfusion measurement to provide treatment before bed sores actually begin. The devices 10 and 300 are hand held devices which are easy to handle and use at any location. The devices 10 and 300 provide a rapid assessment of skin perfusion. The result of the test is displayed in less than one minute, and preferably less than 30 seconds.

Although the invention has been described in detail with reference to a certain preferred embodiment, variations and modifications exist within the scope and spirit of the present invention as described and defined in the following claims.

What is claimed is:

1. A method for evaluating perfusion adjacent a skin surface, the method comprising the steps of:

applying a positive force to a first zone of the skin surface;

applying a negative force to a second zone of the skin surface;

measuring a rate of perfusion in the first zone;

measuring a rate of perfusion in the second zone; and calculating a differential rate of perfusion between the first and second zones of the skin surface to provide an indication of perfusion adjacent the skin surface.

2. The method of claim 14, wherein the step of measuring the rate of perfusion in the first zone includes the step of measuring a temperature of the skin surface in the first zone, the step of measuring the rate of perfusion in the second zone includes the step of measuring a temperature of the skin surface in the second zone, and wherein the step of calculating a differential rate of perfusion includes the step of calculating a differential temperature between the first and second zones of the skin surface.

3. The method of claim 1, further comprising the step of displaying the indication of perfusion.

4. The method of claim 1, wherein the second zone of the skin surface surrounds the first zone.

5. The method of claim 1, wherein the first and second zones of the skin are spaced apart from each other.

6. The method of claim 1, further comprising the step of heating the first and second zones of the skin surface to a base temperature prior to the applying steps.

7. The method of claim 1, further comprising the step of cooling the first and second zones of the skin to a base temperature before the applying steps.

8. A method for evaluating perfusion adjacent a skin surface, the method comprising the steps of:

measuring a reference temperature of the skin surface;

storing the reference temperature;

applying a positive compressive force to the skin surface;

measuring a temperature of the skin surface after the positive compressive force is applied; and calculating a differential temperature between the reference temperature and the temperature after the positive compressive force is applied to provide an indication of perfusion adjacent the skin surface.

9. The method of claim 8, further comprising the step of displaying the indication of perfusion.

10. A method for evaluating perfusion adjacent a skin surface, the method comprising the steps of:

measuring a reference rate of perfusion of the skin surface;

storing the reference rate of perfusion;

applying a positive compressive force to the skin surface;

measuring a second rate of perfusion adjacent the skin surface after the positive compressive force is applied; and calculating a differential rate of perfusion between the reference rate of perfusion and the second rate of perfusion after positive compressive force is applied to provide an indication of perfusion adjacent the skin surface.

11. The method of claim 10, further comprising the step of displaying the indication of perfusion.

* * * * *

UNITED STATES PATENT AND TRADEMARK OFFICE
CERTIFICATE OF CORRECTION

PATENT NO. : 5,769,784　　　　　　　　　　　　　　　　　　　　　　　　Page 1 of 1
DATED     : June 23, 1998
INVENTOR(S) : Barnett et al.

It is certified that error appears in the above-identified patent and that said Letters Patent is hereby corrected as shown below:

Claim 2,
Line 1, change "14" to -- 1 --.

Signed and Sealed this

Twentieth Day of November, 2001

Attest:

*Nicholas P. Godici*

NICHOLAS P. GODICI
*Attesting Officer*　　*Acting Director of the United States Patent and Trademark Office*